(12) United States Patent
Wang

(10) Patent No.: US 8,083,726 B1
(45) Date of Patent: Dec. 27, 2011

(54) ENCAPSULATING CELLS AND LUMEN

(75) Inventor: Edwin Wang, Tustin, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 752 days.

(21) Appl. No.: 11/240,694

(22) Filed: Sep. 30, 2005

(51) Int. Cl.
*A61M 31/00* (2006.01)
*A61F 2/06* (2006.01)
*A61F 2/02* (2006.01)

(52) U.S. Cl. ... 604/506; 623/1.38; 623/1.41; 623/23.75; 424/93.7

(58) Field of Classification Search ............... 604/506; 623/1.38, 1.41, 1.42, 1.49, 23.75; 424/3.7–93.73
See application file for complete search history.

(56) References Cited

U.S. PATENT DOCUMENTS

| | | |
|---|---|---|
| 4,794,931 A | 1/1989 | Yock |
| 5,049,130 A | 9/1991 | Powell |
| 5,100,185 A | 3/1992 | Menke et al. |
| 5,202,745 A | 4/1993 | Sorin et al. |
| 5,291,267 A | 3/1994 | Sorin et al. |
| 5,304,121 A | 4/1994 | Sahatjian |
| 5,321,501 A | 6/1994 | Swanson et al. |
| 5,365,325 A | 11/1994 | Kumasaka et al. |
| 5,459,570 A | 10/1995 | Swanson et al. |
| 5,465,147 A | 11/1995 | Swanson |
| 5,485,486 A | 1/1996 | Gilhousen et al. |
| 5,827,313 A | 10/1998 | Ream |
| 5,957,941 A | 9/1999 | Ream |
| 6,217,554 B1 * | 4/2001 | Green ................. 604/164.01 |
| 6,333,194 B1 | 12/2001 | Levy et al. |
| 6,368,356 B1 | 4/2002 | Zhong et al. |
| 6,558,665 B1 * | 5/2003 | Cohen et al. ............. 424/93.7 |
| 6,692,466 B1 | 2/2004 | Chow et al. |
| 6,818,018 B1 | 11/2004 | Sawhney |
| 6,911,496 B2 | 6/2005 | Rhee et al. |
| 7,457,661 B2 * | 11/2008 | Doty ........................ 604/21 |
| 2003/0073979 A1 * | 4/2003 | Naimark et al. .......... 604/891.1 |
| 2004/0033214 A1 * | 2/2004 | Young et al. .............. 424/93.7 |
| 2004/0181206 A1 | 9/2004 | Chiu et al. |
| 2004/0229786 A1 * | 11/2004 | Attawia et al. ............. 514/12 |
| 2005/0003010 A1 * | 1/2005 | Cohen et al. .............. 424/486 |
| 2005/0015048 A1 | 1/2005 | Chiu et al. |
| 2005/0196377 A1 * | 9/2005 | Ratcliffe et al. ........... 424/78.31 |
| 2006/0083721 A1 * | 4/2006 | Cohen et al. .............. 424/93.7 |
| 2006/0127873 A1 * | 6/2006 | Hoemann et al. ............ 435/2 |
| 2009/0226519 A1 * | 9/2009 | Claude et al. ............... 424/484 |

* cited by examiner

*Primary Examiner* — Nicholas Lucchesi
*Assistant Examiner* — Victoria P Campbell
(74) *Attorney, Agent, or Firm* — Randy Shen; Blakely Sokoloff Taylor & Zafman LLP

(57) ABSTRACT

A method including combining a cellular component with a viability enhancer material wherein the combination will inhibit an interaction between the cellular component and a delivery device; and delivering the cellular component through the delivery device. An apparatus including a delivery cannula having dimensions suitable for percutaneous delivery and a lumen therethrough, wherein a portion of a luminal surface of the cannula includes a coating that is amenable to a cellular component delivered through the delivery cannula. A method including percutaneously introducing a delivery cannula into a blood vessel; advancing a distal portion of the delivery cannula to a treatment site; and delivering a cellular component through a lumen of the delivery cannula, wherein a portion of a luminal surface of the cannula includes a coating that is amenable to a cellular component delivered through the delivery cannula.

9 Claims, 8 Drawing Sheets

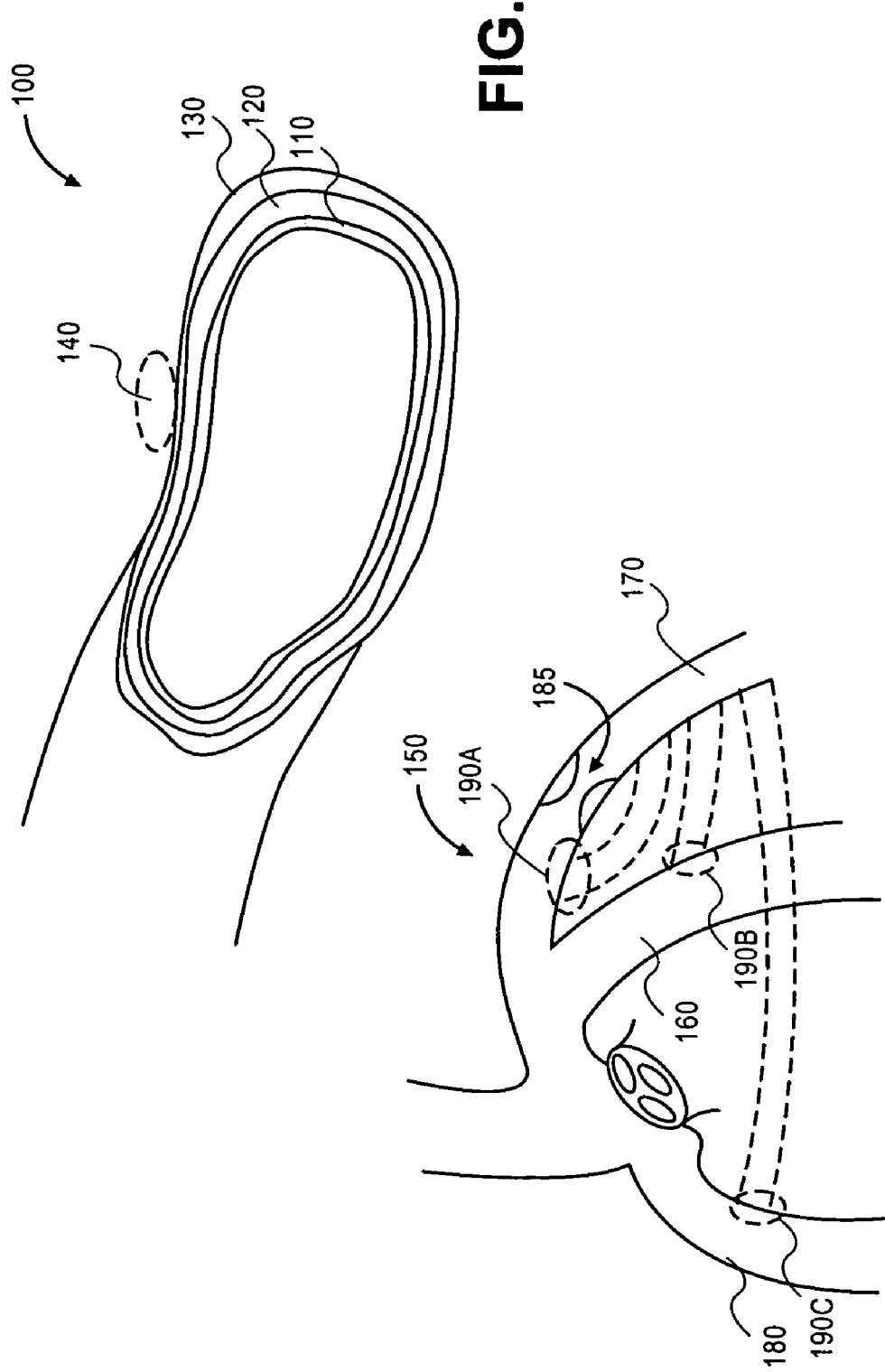

ENCAPSULATING CELLS AND LUMEN

BACKGROUND

1. Field

Resolving ischemia by inducing formation of blood vessels through therapeutic angiogenesis and/or therapeutic angiomyogenesis.

2. Background

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a method and apparatus for delivering agents to help stimulate the natural process of therapeutic angiogenesis to compensate for blood loss due to an occlusion in a coronary and peripheral arteries in order to treat ischemia.

Myocardial infarction (MI) is one form of heart disease that often results from the sudden lack of supply of oxygen and other nutrients. The lack of blood supply is a result of closure of the coronary artery that nourishes a particular part of the heart muscle. The cause of this event is generally caused by arteriosclerosis, "hardening of the arteries," in coronary vessels.

Formerly, it was believed that an MI was caused from a slow progression of closure from, for example, 95 percent then to 100 percent but an MI can also be a result of minor blockages where, for example, there is rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Even though relatively effective systemic drugs exist to treat MI such as ACE-inhibitors and Beta-blockers, a significant portion of the population that experiences a major MI ultimately develop heart failure. An important component in the progression to heart failure is remodeling of the heart due to mechanical forces resulting in uneven stress and strain distribution in the left ventricle. Once an MI occurs remodeling of the heart begins. The principal components of the remodeling event include myocyte death, edema and inflammation, followed by fibroblast infiltration and collagen deposition, and finally scar formation. The principal component of the scar is collagen. Since mature myocytes of an adult are not regenerated the infarct region experiences significant thinning. Myocyte loss is a major etiologic factor of wall thinning and chamber dialation that may ultimately lead to progression of cardiac myopathy. In other areas, remote regions experience hypertrophy (thickening) resulting in an overall enlargement of the left ventricle. This is the end result of the remodeling cascade. These changes in the heart result in changes in the patient's lifestyle and his/her ability to walk and to exercise. These changes also correlate with physiological changes that result in increase in blood pressure and worsening systolic and diastolic performance. Accordingly, it would be desirable to provide a method and apparatus for delivering agents that stabilize ventricles (e.g., the left ventricle) and/or stimulate muscle cell growth.

SUMMARY

According to one embodiment, a method is disclosed. The method includes combining a cellular component with a viability enhancer material such as a hydrogel and delivering the combination through a delivery device. The viability enhancer material is representatively a polymerizable or cross-linkable material and the combination of the viability enhancer material and the cellular component is delivered through the delivery device following the polymerization or cross-linking of the viability enhances material. The combination of the cellular component and the viability enhancer material is such that a combination will inhibit an interaction between the cellular component and the delivery device. In this manner, viability of the cellular component at delivery to a treatment site may be improved because interactions with a delivery, cannula, such as a needle, are minimized.

According to another embodiment, an apparatus is disclosed. In one embodiment the apparatus includes a delivery device having dimensions suitable for percutaneous delivery and a lumen therethrough. The lumen has a sufficient diameter and is configured to deliver a treatment agent. A luminal surface of the delivery device includes a coating having a lower coefficient of friction than the luminal surface of the delivery device. The coated luminal surface improves the viability of a cellular component at a treatment site within a blood vessel by minimizing negative interaction (e.g., decreased shear stress/frictional contact) between the cellular component and an uncoated lumenal surface of the delivery cannula.

BRIEF DESCRIPTION OF THE DRAWINGS

FIG. 1 schematically illustrates a perspective and cross-section view of a blood vessel;

FIG. 2 schematically illustrates a planar cross-sectional view of components of a coronary artery network;

The features of the described embodiments are specifically set forth in the appended claims. However, the embodiments are best understood by referring to the following description and accompanying drawings, in which similar parts are identified by like reference numerals.

DETAILED DESCRIPTION

Figure 3:
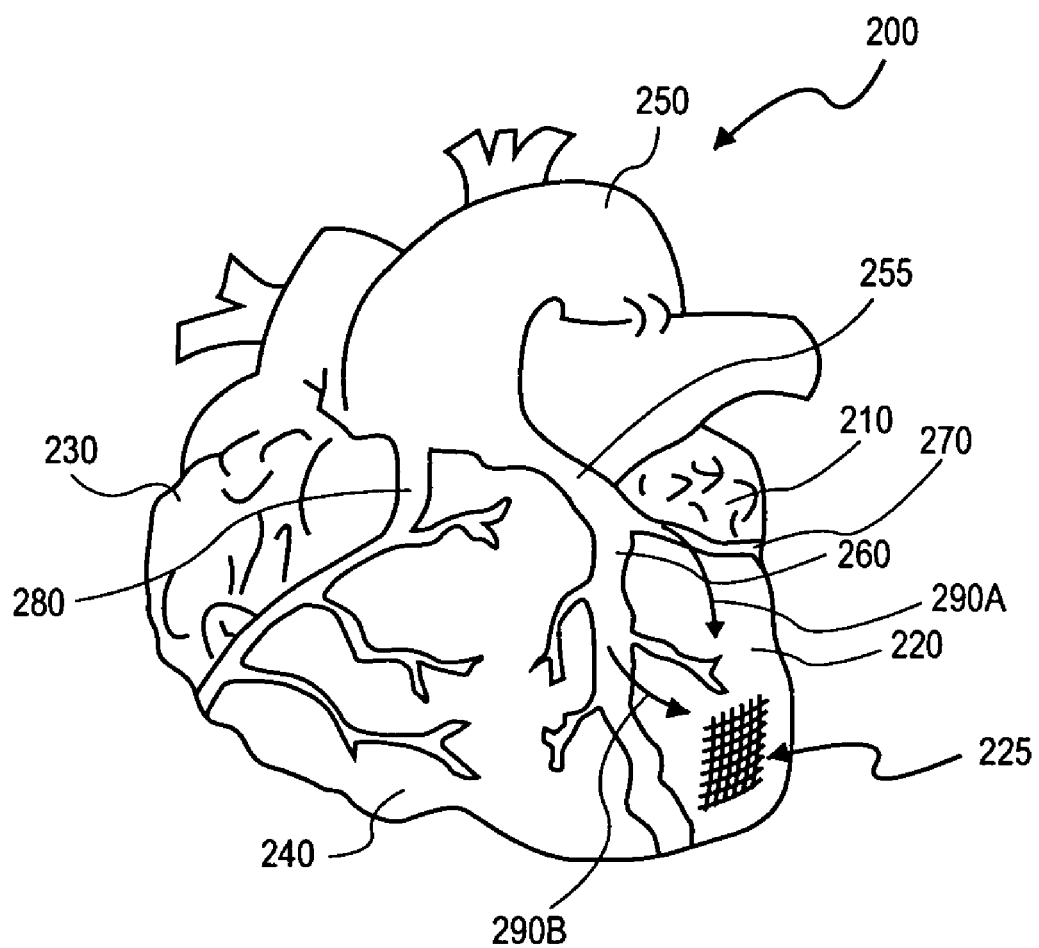
FIG. 3 schematically illustrates a perspective side view of a heart illustrating damage to the left ventricle.

In connection with the description of the various embodiments, the following definitions are utilized:

"Therapeutic angiogenesis" refers to the processes of causing or inducing angiogenesis and arteriogenesis.

"Angiogenesis" is the promotion or causation of the formation of new blood vessels in the ischemic region.

"Arteriogenesis" is the enlargement of pre-existing collateral vessels. The collateral vessels allow blood to flow from a well-perfused region of the vessel into the ischemic region.

"Therapeutic angiomyogenesis" refers to the process of causing or inducing angiomyogenesis.

"Angiomyogenesis" is the promotion or causation of myocytes.

"Ischemia" is a condition where oxygen demand of the tissue is not met due to localized reduction in blood flow caused by narrowing or occlusion of one or more vessels. Narrowing of arteries such as coronary arteries or their branches, is most often caused by thrombosis or via deposits of fat, connective tissue, calcification of the walls, or restenosis due to abnormal migration and proliferation of smooth muscle cells.

"Occlusion" is the total or partial obstruction of blood flow through a vessel.

"Treatment agent" includes agents directed to promoting or causing angiogenesis or angiomyogenesis.

"Carrier" includes a matrix that contains one or more treatment agents. A suitable carrier may take the form of, for example, a nanoparticle (e.g., nanosphere) or microparticle (e.g., microsphere).

Referring to FIG. 1, a non-diseased artery is illustrated as a representative blood vessel. Artery 100 includes an arterial wall having a number of layers. Intimal layer 10 is the innermost layer that includes the endothelium, the subendothelial layer, and the internal elastic lamina. Medial layer 120 is concentrically outward from intimal layer 110 and bounded by external elastic lamina and adventitial layer 130 is the outermost layer. There is no external elastic lamina in a vein. Medial layer 120 (in either an artery or vein) primarily consists of smooth muscle fibers and collagen. Beyond medial layer 120 and adventitial layer 130 lies the extravascular tissue including, adjacent adventitial layer 130 (and possibly including a portion of adventitial layer 130), area 140 referred to as peri-adventitial site (space) or area. Areas radially outward from a peri-adventitial space include connective tissue such as adipose tissue that is most likely located, in terms of areas around the heart, toward the epicardial surface of the heart and myocardial tissue composed of muscle fibers.

FIG. 2 illustrates components of a coronary artery network. In this simplified example, vasculature 150 includes left anterior descending artery (LAD) 160, left circumflex artery (LCX) 170 and right coronary artery (RCA) 180. Sites 190A, 190B, and 190C are preferably in the peri-adventitial space or radially outward from the peri-adventitial space (e.g., in adipose or myocardial tissue). Occlusion 185 is shown in LCX 170. Occlusion 185 limits the amount of oxygenated blood flow through LCX 170 to the myocardium that it supplied, resulting in ischemia of this tissue.

To improve the function of the artery network, it is generally desired to either remove occlusion 185 (for example through an angioplasty procedure), bypass occlusion 185 or induce therapeutic angiogenesis to makeup for the constriction and provide blood flow to the ischemic region (e.g., downstream of occlusion 185). FIG. 2 shows therapeutic angiogenesis induced at sites 190A (associated with LCX 170); 190B (associated with LAD 160); and 190C (associated with RCA 180). By inducing therapeutic angiogenesis at sites 190A, 190B, and 190C, permanent revascularization of the network is accomplished, thus compensating for reduced flow through LCX 170.

In one embodiment, therapeutic angiogenesis is induced and modulated by locally delivering a treatment agent including a cellular component. The treatment agent may be strategically placed, for example, along an occlusion to produce an angiogenic concentration gradient to encourage the specific directional growth or expansion of collateral vessels. For example, in reference to FIG. 2, treatment agents placed at site 190A, above (as viewed) occluded vessel LCX 170 are selected such that, while up-stream, a therapeutic angiogenic or arteriogenic response will encourage growth of collaterals around occlusion 185 meeting up with LCX 170 downstream of the occlusion. Similarly, a treatment agent strategically placed at a location in a region near to LAD 160 (e.g., site 190B) will encourage bridging of collateral vessels, in this case, between LAD 160 and LCX 170. Similar encouragement and bridging may be obtained by strategically placing a treatment agent at a region of RCA 180 (such as site 190C). While the application of therapeutic angiogenesis to alleviating ischemia resulting from a flow limiting obstruction in the LCX is described, those familiar with the art will appreciate that the method described is applicable to the treatment of flow limiting obstructions in other coronary vessels and in the peripheral vasculature.

FIG. 3 shows a schematic view of a portion of a human heart. Representatively, heart 200 includes left atrium 210, left ventricle 220, right atrium 230, and right ventricle 240. In this illustration, various arteries are shown. Included in FIG. 3 are aorta 250, left anterior descending artery (LAD) 260, left circumflex artery (LCX) 270 and right coronary artery (RCA) 280. Site 225, in this embodiment, has been damaged by an MI due to, for example, a lack of blood supply due to a partial closure or closure of LAD 160 or LCX 270 or both. The damage is representatively illustrated at the base of left ventricle 220. Representatively, the damage includes thinning of the muscle tissue of left ventricle 220.

To improve the function of left ventricle 220, therapeutic angiomyogenesis may be induced at myocardial tissue sites 290A and/or 290B. In one embodiment, therapeutic angiomyogenesis is induced by the introduction of a treatment agent including a cellular component through a percutaneous route, such as advancing a catheter into LAD 260 or LCX 270 and delivering a treatment agent beyond the blood vessel into the tissue (e.g., into or onto the adipose or myocardial tissue of left ventricle 220). Alternatively, a catheter may be advanced through the aortic arch, through the right atrium, and into the left ventricle. Using a visualization technique such as fluoroscopy, ultrasound, or magnetic resonance imaging (MRI), a needle tip may be guided into the wall of the left ventricle at a treatment site, representatively at a border zone surrounding site 225.

A. Treatment Agent

In one embodiment, a cellular component for use as or as part of a treatment agent includes, but is not limited to, adult or embyonically-derived stem cells. For example, adult-derived bone marrow cells delivered to ischemic tissue can induce an angiogenic response. Other adult stem cells including, but not limited to, mesenchymal stem cells (MSC), multipotent adult progenator cells (MAPC), and endothelial progenator cells (EPC) may be suitable to induce angiomyogenesis. In another embodiment, suitable cells may be transfected with appropriate gene vectors to become more angiogenic or angiomyogenic and/or to improve the cells survival or preservation in the target medium (e.g., an anti-apoptosis and/or an anti-necrosis factor). In another embodiment, suitable cells may serve as homing agents that tend to attract exogenous cells. Representatively, suitable cells may be transfected with appropriate gene vectors that may function as homing factors. Suitable gene vectors that may serve one or more of the noted functions include, but are not limited to, HIF1alpha, HIF2alpha, SDF-1, IGF, TNF, IL1, PR39, and HGF.

Cellular components, such as the cells noted above, typically have receptors for particular peptide sequences (e.g., cell adhesion ligands) that allow the cellular components to adhere to collagen or other tissue that have receptors. A specific peptide receptor or binding sequence is an arginine-glycine-aspartic acid (RGD) polypeptide. Such receptor allows the cellular components to be delivered in the peri-adventitial space or beyond and be retained in the target tissue to induce or promote angiogenesis and/or angiomyogenesis for collateral formation in the heart as well as in peripheral circulation, such as for applications involving stroke, peripheral arterial disease (PAD), etc.

One concern about introducing a treatment agent including a cellular component such as adult or embryotically-derived stem cells is the viability of the cellular component associated with the introduction technique. It is believed that delivery of a cellular component through a catheter assembly, such as through a delivery cannula (e.g., including a needle) tends to reduce the viability of the cellular component when delivered. For example, one study showed that the cellular component of MSCs were 80 percent viable prior to delivery and yet only 10 percent viable at a treatment site within a ventricle. Accordingly, in one embodiment, the viability and the delivery efficiency of a cellular component within a lumen of the catheter is improved by combining the cellular component prior to delivery with a viability enhancing material. One suitable viability enhancing material is a hydrogel material that may partially or totally encapsulate the cellular component prior to delivery, thus minimizing the viability degradation of the cellular component through a catheter assembly. A suitable hydrogel is typically a water soluble polymer material such as polyethylene glycol material. In one embodiment, a cellular component such as stem cells are partially or totally encapsulated prior to delivery in a phosphatidyl (ethylene glycol) methacrylate (PhosPEG-dMA) hydrogel. A PhosPEG-dMA hydrogel is water soluble and biocompatible. Other suitable hydrogels include, but are not intended to be limited to, polyvinyl alcohol-based, polypropylene fumarate, and polyvinyl pyrolidone photopolymerizing hydrogels and glycosaminoglycans such as hyaluronan and related polysaccharides. Suitable hydrogels are biodegradable. These hydrogels can encapsulate cells and temporarily immobilize the cells. The hydrogel may be rapidly digested by enzymes in a patient leaving viable cells at a treatment site. A solution of hydrogel viability enhancing material and cellular component will be extremely lubricious and tend to minimize the shear forces to which the cellular component might be exposed during hand or pressured pump delivery if introduced without the hydrogel.

In one embodiment, the hydrogel encapsulating the cellular component is polymerized or cross-linked before the combination of cellular component and hydrogel are introduced to a delivery device. A PhosPEG-dMA hydrogel is also cross-linkable permitting a control of a dissolution rate, such as including an amount of a cross-linking agent to establish a gradient for dissolution of the polymer and release of the cellular component (e.g., a sustained release composition). In one embodiment, a suitable cross-linking agent is an agent that relies on chemical means for cross-linking of polymer such as a PhosPEG-dMA polymer. One such chemical cross-linking agent is a naturally occurring agent such as genipin. Another suitable chemical cross-linking agent is a synthetic agent such as a polyepoxy. An example of a polyepoxy is DENACOL™, commercially available from Nagase & Company of Osaka, Japan. In addition to a chemical cross-linking agent, another suitable cross-linking agent to cross-link a PhosPEG-dMA polymer to form a hydrogel is a photo-initiated cross-linker. Suitable photo-initiated cross-linking agents include, but are not intended to be limited to, agents that respond to ultraviolet (UV) or other radiation. Examples of such a photoinitiator and cross-linking agent are benzophenone or Photomer 51,2,2-dimethoxy-2-phenylacetophenone, available through Aldrich catalog #23, 985-2 and #19, 611-8, respectively, or Photomer 6217, a proprietary aliphatic urethane-acrylate oligomer blended with 30 percent tripropylene glycol diacrylate, commercially available from Cognis Corp. Cross-linking of a hydrogel such as hyaluronan can be achieved with di-vinyl sulfone to obtain a jellylike fluid. Di-vinyl sulfone and each of Photomer 51 and Photomer 6217 preferentially react with the hydroxyl groups of the hyaluronan molecules. The biocompatibility of crosslinked hyaluronan is virtually identical to that of hyaluronan.

A suitable dosage of a cellular component in the context of stimulating or promoting angiomyogenesis or angiogenesis is a dosage on the order of three millimeters (mL) to 20 mL of a stem cell such as HMSCs. It is appreciated that a delivery dose may vary depending on the method of delivery and the location of delivery. Other factors include the type of cellular component that is delivered and the location of the delivery may dictate the dosage amount.

In one embodiment, the method of the treatment agent including a cellular component partially or completely encapsulated in a viability enhancing material such as a cross-linked (partially or preferably totally) PhosPEG-dMA may be delivered percutaneously, such as by way of catheter/needle delivery. Suitable delivery mechanisms include delivery of treatment agent and isotonic saline solution (e.g., including an isotonic saline solution of an encapsulated cells such as stem cells). In another embodiment, matrices or gels that encapsulate a cellular component may include various factors, such as homing factors and anti-apoptosis factors, so that when cells are delivered in these matrices or gels, the matrices or gels have the beneficial factor dispersed therein, for example, a protein (e.g., SDF-1) or a peptide (e.g., PR11, PR39). Beneficial factors dispersed in matrices or gels under treatment agent may be as an alternative to transfecting such factors into a cell of the treatment agent or in addition to transfecting such factor into a cells treatment agent.

In the above embodiments, encapsulation of a cellular component is described. It is appreciated that encapsulation may also be utilized with other treatment agents including, but not limited to, protein therapeutics, antigens, and liposome-mediated genes that may be delivered with a cellular component (including but not limited to encapsulation with a cellular component) or separately.

In the above embodiments, a treatment agent is described including a cellular component. Such a treatment agent may be introduced, through percutaneous catheter delivery, to a remote blood vessel, such as a coronary artery or vein. The partial or total encapsulation of the cellular component in a viability enhancing material such as a PhosPEG-dMA gel tends to improve the viability of the cellular component at the treatment site. Such intra-coronary introduction may be either with flow or in a retrograde fashion. Alternatively, the composition may be introduced beyond a blood vessel lumen into extravascular tissue including adjacent adventitial layer 130 (see FIG. 1) or in peri-adventitial space or area by advancing a needle through a blood vessel such as a coronary artery. In another embodiment, a delivery catheter may be introduced into a blood vessel (e.g., a femoral artery) and fed through the aortic arch into the left ventricle. The left ventricle may be punctured at or adjacent to a treatment site and the treatment agent delivered into the tissue of the myocardium.

B. Catheter Assembly

In another embodiment, an apparatus (a catheter assembly) is described for accurately locating a treatment agent at a location in a blood vessel (preferably beyond the media layer) or in a peri-adventitial space adjacent to a blood vessel, or areas radially outward from a peri-adventitial space including at tissue locations such as the tissue of the myocardium. It is appreciated that a catheter assembly is one technique for introducing treatment agents and the following description is not intended to limit the application or placement of the treatment agents described above.

Figure 4:
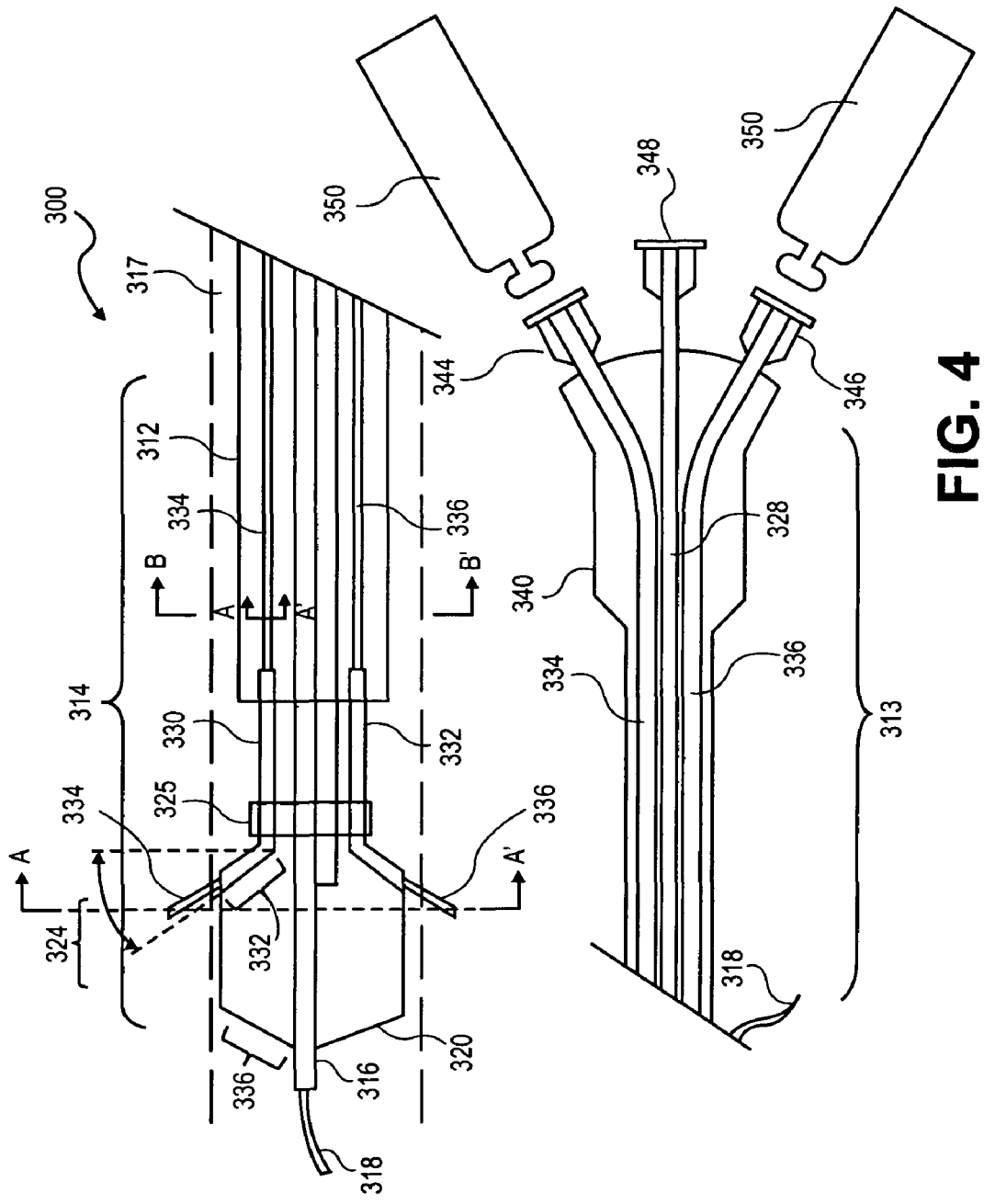
FIG. 4 is a simplified cross-sectional view of an embodiment of a substance delivery apparatus in the form of a catheter assembly having a balloon and a therapeutic substance delivery assembly.

Referring now to the drawings, FIG. 4 illustrates one embodiment of a delivery apparatus. In general, the delivery apparatus provides a system for delivering a substance, such as a treatment agent including an encapsulated (partially or totally) cellular component possibly as a sustained release composition, to or through a desired area of a blood vessel (a physiological lumen) or tissue in order to treat a localized area of the blood vessel or to treat a localized area of tissue possibly located adjacent to the blood vessel. The delivery apparatus is similar in certain respects to the delivery apparatus described in commonly-owned, U.S. patent application Ser. No. 09/746,498 (filed Dec. 21, 2000), titled "Local Drug Delivery Catheter with Retractable Needle," of Steward et al.; U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al. Each of these applications is incorporated herein by reference. The delivery apparatus described is suitable, in one embodiment, for a percutaneous delivery of a treatment agent where a desired form of the treatment agent is introduced through a single catheter needle.

Referring to FIG. 4, the delivery apparatus includes catheter assembly 300, which is intended to broadly include any medical device designed for insertion into a blood vessel or physiological lumen to permit injection and/or withdrawal of fluids, to maintain the patency of the lumen, or for any other purpose. In one embodiment, catheter assembly 300 is defined by elongated catheter body (cannula) 312 having proximal portion 313 and distal portion 314. In one embodiment, proximal portion 313 may reside outside a patient during a procedure while distal portion 314 is placed at a treatment site, for example, within coronary blood vessel 317.

Catheter assembly 300 includes catheter body 312 having a lumen therethrough extending from proximal portion 313 to distal portion 314. In this example, guidewire cannula 316 is formed within catheter body 312 for allowing catheter assembly 300 to be fed and maneuvered over a guidewire (guidewire 318 shown at this point within a lumen of guidewire cannula 316). Guidewire cannula 316 may extend from proximal portion 313 to distal portion 314, thus describing an over the wire (OTW) assembly. In another embodiment, typically described as a rapid exchange (RX) type catheter assembly, guidewire cannula 316 extends only through a portion of catheter body 312, for example, beginning and ending within distal portion 314. An RX type catheter assembly is shown. It is appreciated that guidewire 318 may be retracted or removed once catheter assembly 300 is placed at a region of interest, for example, within a blood vessel (e.g., artery or vein).

In the embodiment of FIG. 4, catheter assembly 300 includes balloon 320 incorporated at distal portion 314 of catheter assembly 300. Balloon 320 is an expandable body in fluid communication with inflation cannula 328 disposed within catheter body 312. Inflation cannula 328 extends from balloon 320 within distal portion 314 through inflation port 348 at proximal portion 313 (e.g., at a proximal end of catheter assembly 300). Inflation cannula 328 is used to deliver a fluid to inflate balloon 320.

In the embodiment shown in FIG. 4, balloon 320 is in an expanded or inflated state that occludes blood vessel 317. Balloon 320 is selectively inflatable to dilate from a collapsed configuration to a desired or controlled expanded configuration. Balloon 320 can be selectively inflated by supplying a fluid (e.g., liquid) into a lumen of inflation cannula 328 at a predetermined rate of pressure through inflation port 348. Likewise, balloon 320 is selectively deflatable to return to a collapsed configuration or deflated profile.

In one embodiment, balloon 320 can be defined by three portions: distal taper wall 326, medial working length 324, and proximal taper wall 322. In one embodiment, proximal taper wall 322 can taper at any suitable angle θ, typically between about 15° to less than about 90°, when balloon 320 is in an expanded (inflated) configuration.

Balloon 320 can be made from any suitable material, including, but not limited to, polymers and copolymers of polyolefins, polyamides, polyester and the like. The specific material employed should be compatible with inflation or expansion fluid and must be able to tolerate the pressures that are developed within balloon 320. One suitable material is an elastomeric nylon such as PEBAX™, a condensation polymerized polyether block polyamide. PEBAX™ is a trademark of ATOCHEM Corporation of Puteaux, France. Other suitable materials for balloon 320 include, but are not limited to, a biocompatible blend of polyurethane and silicone, or a styrenic block copolymer (SBC) or blend of SBCs. Distal taper wall 326, medial working length 324, and proximal taper wall 322 can be bound together by seams or be made out of a single seamless material. A wall of balloon 320 (e.g., at any of distal taper wall 326, medial working length 324 and/or proximal taper wall 322) can have any suitable thickness so long as the thickness does not compromise properties that are critical for achieving optimum performance. Relevant properties include, but are not limited to, high burst strength, low compliance, good flexibility, high resistance to fatigue, the ability to fold, the ability to cross and recross a desired region of interest or an occluded region in a physiological lumen and low susceptibility to defects caused by handling. By way of example, not limitation, a suitable thickness of a balloon wall can be in the range of about 0.0005 inches to 0.002 inches, the specific specifications depending on the procedure for which balloon 320 is to be used and the anatomy and size of the target lumen in which balloon 320 is to be inserted.

Balloon 320 may be inflated by the introduction of a fluid (e.g., liquid) into inflation cannula 328 (through inflation port 348 at a point outside a physiological lumen). Liquids containing therapeutic and/or diagnostic agents may be used to inflate balloon 320. In one embodiment, balloon 320 may be made of a material that is permeable to such therapeutic and/or diagnostic agents. To inflate balloon 320, a suitable fluid may be supplied into inflation cannula 328 at a predetermined pressure, for example, between about one and 20 atmospheres (atm). A specific pressure depends on various factors, such as the thickness of the balloon wall, the material of which balloon 320 is made, the type of substance employed, and the flow rate that is desired.

Catheter assembly 300, in the embodiment shown in FIG. 4 also includes delivery cannula 330 and delivery cannula 332 each connected to proximal taper wall 322 of balloon 320 and extending at a proximal end, in one embodiment, into a portion of catheter body 312 of catheter assembly 300. Representatively, a suitable length for delivery cannula 330 and delivery cannula 332 is on the order of three to 6.5 centimeters (cm). Delivery cannula 330 and delivery cannula 332 can be made from any suitable material, such as polymers and copolymers of polyamides, polyolefins, polyurethanes, and the like. Catheter assembly 300, in this view, also includes needle 334 and needle 336. Needle 334 and needle 336 extend from distal portion 314 to proximal portion 313 of catheter assembly 300. At distal portion 314, needle 334 is slidably disposed through a lumen of delivery cannula 330 and needle 336 is slidably disposed through a lumen of delivery cannula 332. Thus, a dimension of delivery cannula 330 and delivery cannula 332 are each selected to be such to allow a delivery device such as a needle to be moved therethrough. Representatively, delivery cannula 330 has an inner diameter (lumen diameter) on the order of 0.002 inches to 0.020 inches (e.g., 0.0155 inches) and an outer diameter on the order of 0.006 inches to 0.05 inches (e.g., 0.0255 inches). FIG. 4 shows catheter assembly 300 with each of needle 334 and needle 336 deployed in an extended configuration, i.e., extending from an end of delivery cannula 330 and delivery cannula 332, respectively. In a retracted configuration, the needles retract proximally into the delivery cannula lumens.

Figure 5:
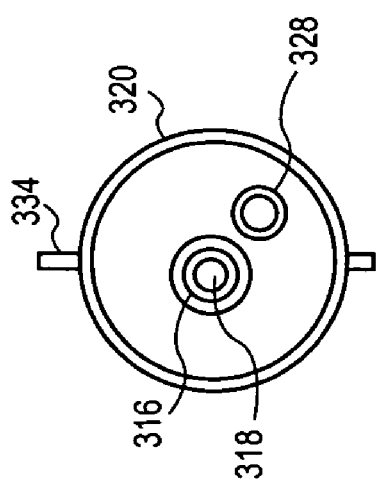
FIG. 5 schematically illustrates a planar cross-sectional view of the substance delivery apparatus of FIG. 4 through line A-A'.

FIG. 5 shows a cross-section through line A-A' of FIG. 4. From this view, catheter assembly 300 includes two needles (and two delivery cannulas). FIG. 5 shows needle 334 and needle 336. Representatively, delivery cannula 330 and delivery cannula 332 may be spaced either radially and/or circumferentially from each other, for example, between 45° and 180° apart. FIG. 4 and FIG. 5 shows delivery cannula 330 and needle 334 circumferentially spaced about 180° from delivery cannula 332 and needle 336. In other embodiments, a catheter assembly may include one or more needles. Representatively, a suitable catheter assembly may include two needles such as needle 334 and another needle (e.g., needle 336) adjacent one another.

FIG. 4 shows delivery cannula 330 and delivery cannula 332 each connected to an exterior surface of balloon 320. Specifically, a distal end of each of delivery cannula 330 and delivery cannula 332 extend to a point equivalent to or less than a length of proximal taper wall 322 of balloon 320. One suitable technique for connecting delivery cannula 330 or delivery cannula 332 to balloon 320 is through an adhesive. A suitable adhesive includes a cyanocrylate (e.g., LOCTITE 414™) adhesive, particularly where the balloon material is a PEBAX™ material.

Catheter assembly 300 in the embodiment shown in FIG. 4 also includes sheath ring 325. Sheath ring 325 is positioned over, in this embodiment, guidewire cannula 316, inflation cannula 328, delivery cannula 330, and delivery cannula 332, respectively. In one embodiment, sheath ring 325 functions to inhibit delamination of the delivery cannulas from proximal taper wall 322 of balloon 320 and, where thermally sealed to the various cannulas may reduce the spacing (on a proximal side of sheath ring 325) of the cannulas. Thus, a distal end of sheath ring 325 is placed, in one embodiment, at a point immediately proximal to where a delivery cannula will rotate, bend or plicate in response to the expansion or inflation of balloon 320. In one embodiment, sheath ring 325 is a biocompatible material that is capable of connecting to (e.g., bonding to) a material for balloon 320 and to a material for each of the noted cannulas that it surrounds. Representatively, a body of sheath ring 325 has a length from a proximal end to a distal end on the order of 0.25 millimeters (mm) to 0.75 mm, such as 0.5 mm.

One way to form catheter assembly 300 including sheath ring 325 is to initially connect (e.g., bond) balloon 320 at a distal end to guidewire cannula 316. Balloon 320 is also connected (e.g., bonded) at a proximal end to guidewire cannula 316 and inflation cannula 328. Once balloon 320 is sealed at each end, balloon 320 is inflated. The delivery cannulas are aligned on inflated balloon 320 with a distal end at reference point corresponding to a distal end of proximal taper wall 322 of balloon 320. Distal ends of the delivery cannulas may be tapered to approximate or match a plane defined by medial working length 324 of balloon 320 when balloon 320 is in an inflated state. The delivery cannulas may then be glued or affixed to balloon 320 through an adhesive such as a cyanoacrylate adhesive. Next, sheath ring 325 is loaded (advanced proximal to distal) onto a proximal end of balloon 320 and the cannulas of catheter assembly 300 (e.g., guidewire cannula 316, inflation cannula 328, delivery cannula 330 and delivery cannula 332. A material of sheath ring 325 of a polymer such as PEBAX 40D™ may be connected to balloon 320 and the delivery cannulas by a thermal seal process. As an alternative to a thermal seal process for connecting sheath ring 325, sheath ring 325 may be connected to balloon 320 and the delivery cannulas by an adhesive, such as cyanoacrylate adhesive.

As noted above, each delivery cannula (e.g., delivery cannula 330, delivery cannula 332) plicates or bends distal to sheath ring 325 with the inflation of balloon 320. Thus, the path to be traveled by each needle (e.g., needle 334 and needle 336) includes this bend or plication. To facilitate a travel through a bend or plication region in each delivery cannula and to inhibit puncturing of the respective delivery cannula, each delivery cannula may include a deflector disposed along an interior wall. Representatively, a suitable deflector includes a ribbon of thin, generally flexible and generally resilient material (e.g., thickness on the order of about 0.0005 inches to about 0.003 inches and width on the order of about 0.005 inches and 0.015 inches). Suitable deflector materials, dimensions and connections within a catheter assembly are described in commonly-owned, U.S. patent application Ser. No. 09/746,498 (filed Dec. 21, 2000), titled "Local Drug Delivery Catheter with Retractable Needle," of Steward et al.; U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al.

Figure 6:
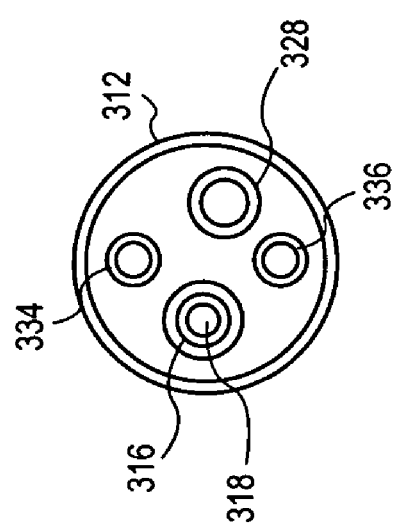
FIG. 6 schematically illustrates a planar cross-sectional view of the substance delivery apparatus of FIG. 4 through line B-B'.

FIG. 6 shows a cross-section through line B-B' of FIG. 4. FIG. 6 shows catheter body 312 as a cannula including a lumen therethrough. Inside the lumen of catheter body 312 is needle 334 and needle 336. Also disposed in a lumen of catheter body 312 is inflation cannula 328 and guidewire cannula 316. Disposed within a lumen of guidewire cannula 316 is guidewire 318.

Figure 7:
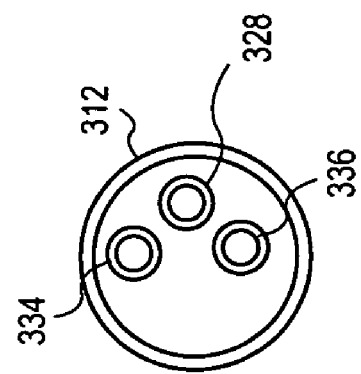
FIG. 7 schematically illustrates a cross-sectional view of the distal section of the substance delivery apparatus of FIG. 4 through line C-C'.

FIG. 7 shows a cross-section through line C-C' of FIG. 4, illustrating a cross-section through proximal portion 313 of catheter assembly 300. FIG. 7 shows catheter body 312 having a lumen therethrough. Disposed within the lumen of catheter body 312 is needle 334 and needle 336. A lumen of catheter body 312, at this cross-section, also includes inflation cannula 328. Guidewire cannula 316, in this one embodiment, does not extend proximally as far as line C-C'. It is appreciated that the cross-sectional area of catheter body 312 may be minimized (minimum profile) at proximal portion 313 of catheter assembly 300 because fewer articles are accommodated in a lumen of catheter body 312 (e.g., at this point guidewire cannula 316 is not present).

Referring again to FIG. 4, proximal portion 313 of catheter assembly 300 is intended, in one embodiment, to reside outside a patient while the remainder of catheter assembly 300 is percutaneously introduced into, for example, the cardiovascular system of a patient via a brachial, a radial or a femoral artery. In this embodiment, proximal portion 313 of catheter assembly 300 includes hub 340. Hub 340 includes needle 334 and needle 336, and inflation cannula 328. In one embodiment, relative to the materials for the various cannulas described, a housing of hub 340 is a hard or rigid polymer material, e.g., a polycarbonate or acrylnitrile bubadiene styrene (ABS). A distal end of hub 340 has an opening to accommodate a proximal end of catheter body 312. Hub 340 also has a number of cavities at least partially therethrough (extending in a distal to proximal direction) to accommodate needle 334 and needle 336, and inflation cannula 328. A proximal portion of hub 340 flares to separate a spacing between the needles, and inflation cannula 328.

FIG. 4 shows a proximal end of needle 334 and needle 336 each connected (e.g., through an adhesive) to respective injection port 344 and injection port 346. In one embodiment, each injection port includes a luer fitting for conventional syringe attachment. Each injection port allows for the introduction of treatment agent 350, including but not limited to a drug or cellular component (e.g., stem cell). It is appreciated that treatment agent 350 introduced at injection portion 344 and injection port 346 may be the same or different (e.g., a treatment agent including a cellular component in a hydrogel that will be released immediately versus a treatment agent including a cellular component in a hydrogel in which the cellular component will be released over time (sustained release); a treatment agent including a cellular component versus a treatment agent including a drug, etc.). In this embodiment, inflation cannula 328 terminates at the distal end of balloon inflation port 348.

In one embodiment, catheter assembly 300 also includes or can be configured to include an imaging assembly. Suitable imaging assemblies include ultrasonic imaging assemblies, optical imaging assemblies, such as an optical coherence tomography (OCT) assembly, magnetic resonance imaging (MRI). One embodiment of catheter assembly 300 illustrated in FIG. 4 may include an OCT imaging assembly.

OCT uses short coherent length light (typically with a coherent length of about 10 to 100 microns) to illuminate the object (e.g., blood vessel or blood vessel walls). Light reflected from a region of interest within the object is combined with a coherent reference beam. Interference occurs between the two beams only when the reference beam and reflective beam have traveled the same distance. One suitable OCT setup may be similar to ones disclosed in U.S. Pat. Nos. 5,465,147; 5,459,570; 5,321,501; 5,291,267; 5,365,325; and 5,202,745. A suitable optical assembly for use in conjunction with a catheter assembly is made with fiber optic components that, in one embodiment, can be passed through the guidewire lumen (e.g., guidewire cannula 316 of FIG. 4). Light having a relatively short coherence length, $l_c$ (given by $l_c=C/\Delta f$, where $\Delta f$ is the spectral bandwidth) is produced by light source 380 (e.g., incandescent source, laser source or light emitting diode of suitable wavelength) and travels through a 50/50 coupler 382 where it is divided into two paths. One path goes to the blood vessel to be analyzed and the other path goes to a moveable reference mirror. The probe beam reflected from the blood vessel and the reference beam reflected from the reference mirror are combined at the coupler and sent to a detector. The optical path traversed by the reflected probe beam and the reference beam are matched to within one coherence length such that coherent interference can occur upon recombination at the coupler.

A phase modulator produces a temporal interference pattern (beats) when recombined with the reference beam. The detector measures the amplitude of the beats. The amplitude of the detected interference signal is the measure of the amount of light scattered from within a coherence gate interval inside, in this case, the blood vessel that provides equal path lengths for the probe and reference beams. Interference is produced only for light scattered from the blood vessel which has traveled the same distance as light reflected from the reference mirror.

In one embodiment, the optical fiber portion of the OCT imaging system can be inserted in a lumen of a guidewire cannula of an over the wire catheter with the guidewire lumen terminating at the imaging wire coupling. The body of the guidewire cannula (e.g., guidewire cannula 316 of catheter assembly 300 of FIG. 4) and the body of the balloon assembly (e.g., balloon 320 in FIG. 4) should be transparent at the distal end to allow optical imaging (e.g., through the body of balloon 320). Thus, once the catheter assembly is placed, at a desired location within, for example, a blood vessel, guidewire 318 may be removed and replaced with an optical fiber. In a catheter assembly such as illustrated in FIG. 4, the replacement of the guidewire with an optical fiber is done, in one embodiment, at low inflation pressure of balloon 320.

Where an optical fiber is substituted for a guidewire, the dimensions of a catheter does not have to be modified. Optical fibers having an outer diameter of 0.014, 0.018, or 0.032 inches (0.36, 0.46, or 0.81 mm, respectively) are suitable for current guidewire lumens. Other imaging components (e.g., fiber rotator, imaging screen, OCT system components, etc.) may be connected to the optical fiber as it extends out proximal portion of the catheter assembly 300 (see FIG. 4). Such components include, but are not limited to, a drive coupling that provides rotation and forward/reverse movement of the optical fiber; a detector, and an imaging screen.

In another embodiment, the imaging assembly is based on ultrasonic technology. Ultrasonic systems are referenced in U.S. Pat. Nos. 4,794,931; 5,100,185; 5,049,130; 5,485,486; 5,827,313; and 5,957,941. In one example, an ultrasonic imaging assembly, representatively including an ultrasonic transducer, may be exchanged for a guidewire through a lumen of a guidewire cannula such as described above with reference to the first OCT embodiment. In another embodiment, a guidewire and ultrasonic transducer "share" a common lumen of an imaging cannula similar to the embodiment described with reference to FIG. 9 and the accompanying text. In either example, imaging of, for example, a blood vessel will take place through the balloon. In the case of ultrasonic imaging, the balloon and guidewire cannula need not be transparent.

Figure 8:
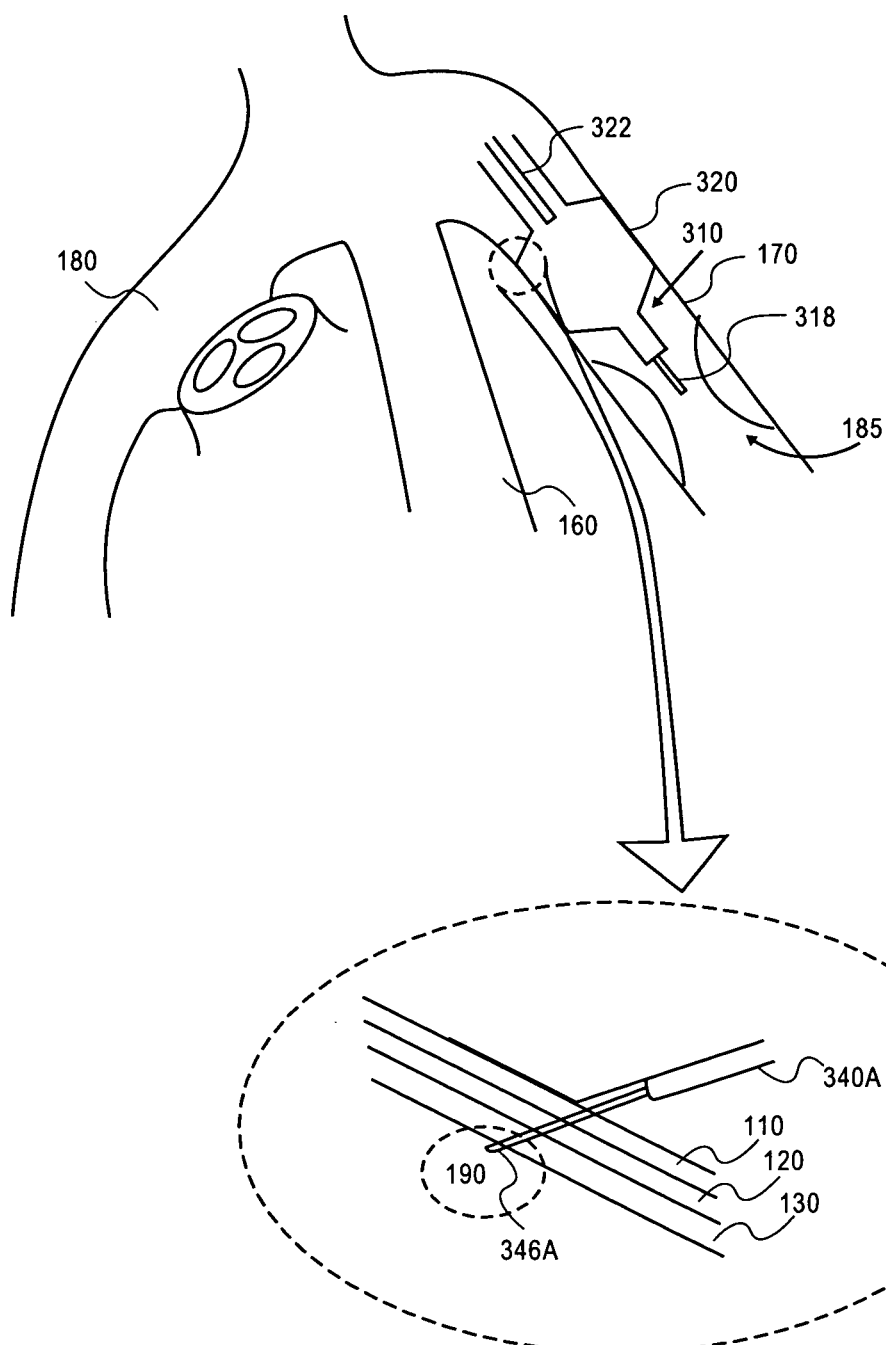
FIG. 8 schematically illustrates the portion of coronary artery network of FIG. 2 having a catheter assembly introduced therein.
Figure 9:
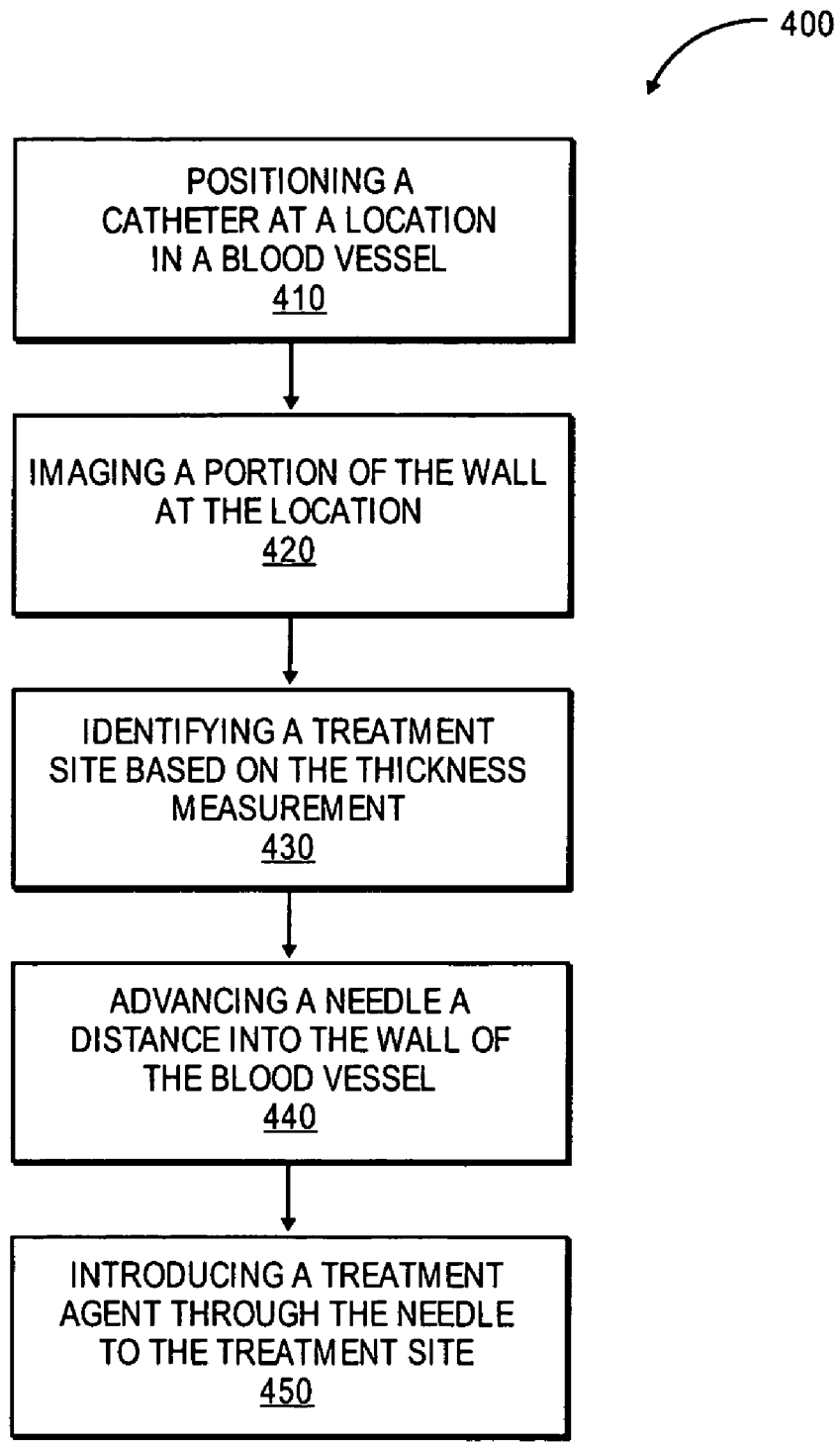
FIG. 9 presents a block diagram for introducing a treatment agent.

The catheter assembly described with reference to FIG. 4 may be used to introduce a treatment agent such as described above at a desired location. FIG. 8 illustrates one technique. FIG. 9 presents a block diagram of one technique. With reference to FIGS. 8 and 9 and catheter assembly 300 of FIG. 4, in a one procedure, guidewire 318 is introduced into, for example, an arterial system of the patient (e.g., through the femoral artery) until the distal end of guidewire 318 is upstream of the narrowed lumen of the blood vessel (e.g., upstream of occlusion 185). Catheter assembly 300 is mounted on the proximal end of guidewire 318 and advanced over the guidewire 318 until catheter assembly 300 is position as desired. In the example shown in FIG. 8, catheter assembly 300 is positioned so that balloon 320 and delivery cannula 330 are upstream of the narrowed lumen of LCX 170 (block 410). Angiographic or fluoroscopic techniques may be used to place catheter assembly 300. Once balloon 320 is placed and subject to low inflation pressure, guidewire 318 is removed and replaced in one embodiment with an optical fiber. In the catheter assembly shown in FIG. 9, the imaging portion of an imaging device (e.g., OCT, ultrasonic, etc.) may be within the imaging lumen as the catheter is positioned. Once positioned, in this case upstream of occlusion 185, the imaging assembly is utilized to view the blood vessel and identify the various layers of the blood vessel (block 420).

The imaging assembly provides viewable information about the thickness or boundary of the intimal layer 110, media layer 120, and adventitial layer 130 of LCX 170 (see FIG. 1). The imaging assembly may also be used to measure a thickness of a portion of the blood vessel wall at the location, e.g., the thickness of the various layers of LCX 170.

LCX 170 is viewed and the layer boundary is identified or a thickness of a portion of the blood vessel wall is imaged (and possibly measured) (block 420). The treatment site may be identified based on the imaging (and possible measuring) (block 430). In one example, the treatment site is a peri-adventitial site (e.g., site 190) adjacent to LCX 170. At this point, balloon 320 is dilated as shown in FIG. 4 by, for example, delivering a fluid to balloon 320 through inflation cannula 328. The inflation of balloon 320 causes delivery cannula 330 to move proximate to or contact the blood vessel wall adjacent to the treatment site. Needle 334 is then advanced a distance into the wall of the blood vessel (block 440). A real time image may be used to advance needle 334. Alternatively, the advancement may be based on a measurement of the blood vessel wall or layer boundary derived from an optical image.

In the embodiment shown in FIG. 8, needle 334 is advanced through the wall of LCX 170 to myocardial tissue at peri-adventitial site 190. Needle 334 is placed at a safe distance, determined by the measurement of a thickness of the blood vessel wall and the proximity of the exit of delivery cannula 330 to the blood vessel wall. Once in position, a treatment agent, such as a treatment agent including a cellular component, is introduced through needle 334 to the treatment site (e.g., peri-adventitial site 190) (block 450).

In the above described embodiment of locating a treatment agent within or beyond a blood vessel wall (e.g., at a peri-adventitial site), it is appreciated that an opening is made in or through the blood vessel. In same instances, it may be desirable to plug or fill the opening following delivery of the treatment agent. This may be accomplished by introduction of cyanoacrylate or similar material that will harden on contact with blood.

In the above embodiments, an illustration and method was described to introduce a treatment agent at a peri-adventitial site and to a myocardial tissue site. It is appreciated that the treatment agent may be introduced to a portion of the wall of the blood vessel. In another embodiment, the introduction is at a point beyond the media layer (e.g., beyond media layer 120 in FIG. 1) to the adventitial layer (e.g., adventitial layer 130 in FIG. 1). Further, in the above embodiments, reference to introduction of a treatment agent including a cellular component is made to induce and/or modulate therapeutic angiogenesis and/or therapeutic angiomyogenesis. It is appreciated that additional therapeutic treatment agents (e.g., drugs, growth factors, inflammation inducing agents, etc.) may additionally be introduced along with or separate from a treatment agent including a cellular component where desired.

Still further, in the catheter assembly described with reference to FIG. 4, a single balloon catheter assembly is illustrated. It is appreciated that a suitable catheter assembly may include multiple balloons (e.g., in series or tandem). Representative multiple balloon assemblies are described in commonly-owned, U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al. Each balloon in a multiple balloon catheter assembly may function in a similar way (e.g., to deliver a treatment agent to a wall of a blood vessel or beyond a wall of a blood vessel) or differently (e.g., one balloon to deliver a stent a second balloon to deliver a treatment agent) In the case of co-injection of precursors that interact, combine, or react with one another, a first treatment agent may be introduced off of one balloon, while a second treatment agent may be introduced off a second adjacent balloon.

In the embodiment described with reference to FIGS. 4-9, a catheter assembly for introducing a cellular component at a treatment site beyond a blood vessel is described. Such technique may be used to promote and/or modulate angiogenesis or angiomyogenesis. In another embodiment, it may be desired to introduce a cellular component within a blood vessel (i.e., an intra-coronary introduction). Such technique may be used to deliver a cellular component that will diffuse through the blood vessel into capillaries and promote and/or modulate angiogenesis or angiomyogenesis. Alternatively, a cellular component may be introduced that promotes the growth of endothelial cells or a restoration of an endothelial layer where, for example, a blood vessel has been damaged due to an angioplasty procedure.

Figure 10:
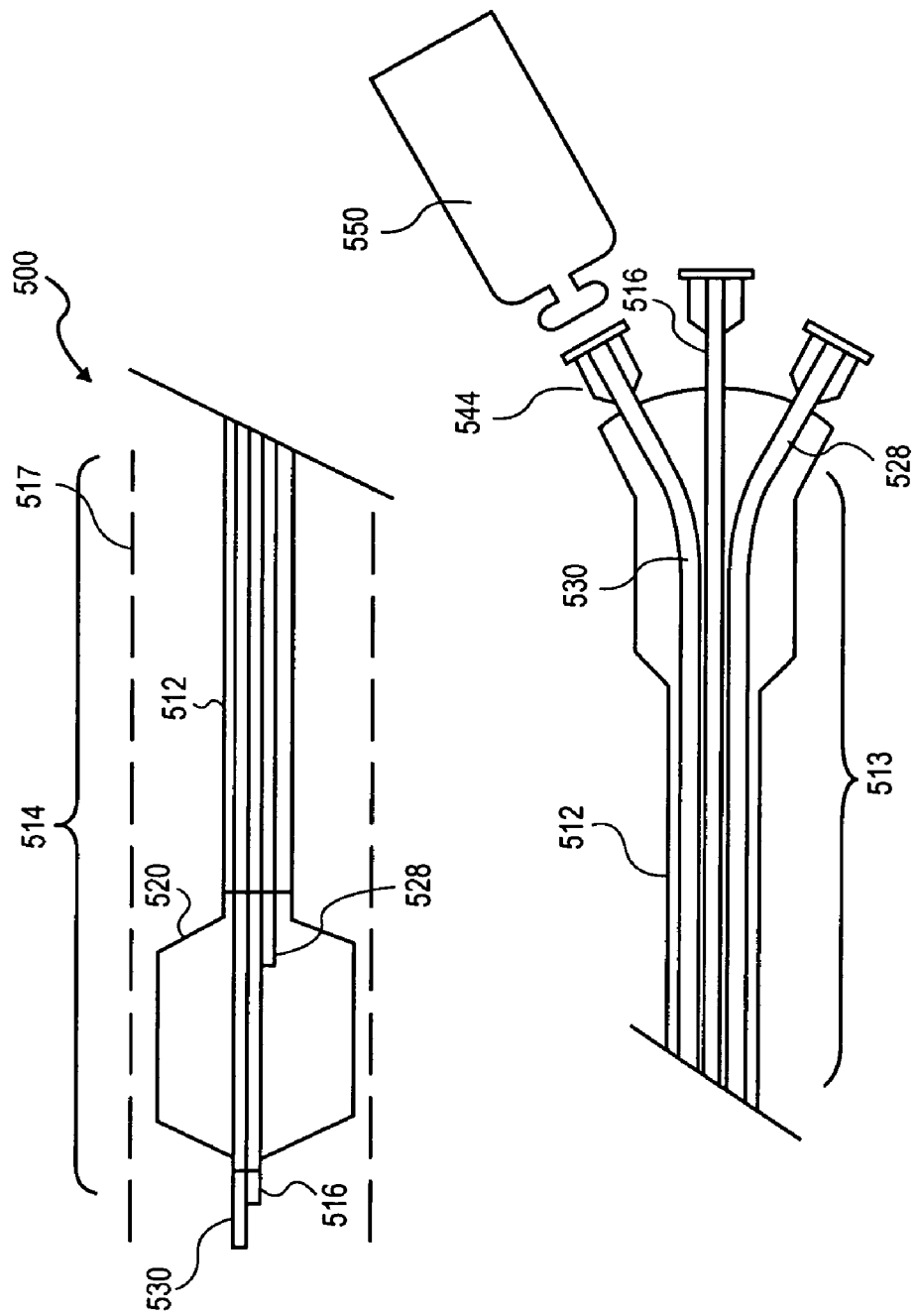
FIG. 10 schematically illustrates a simplified cross-sectional view of a second embodiment of a substance delivery apparatus in the form of a catheter assembly having a balloon and a treatment agent delivery assembly.

FIG. 10 shows blood vessel 517 having catheter assembly 500 disposed therein. Catheter assembly 500 includes proximal portion 513 and distal portion 514. Proximal portion 513 may be external to blood vessel 517 and to the patient. Representatively, catheter assembly 500 may be inserted through a femoral artery and through, for example, a guide catheter and with the aid of a guidewire to a location in the vasculature of a patient. That location may be, for example, a coronary artery. FIG. 10 shows distal portion 514 of catheter assembly 500 positioned at a treatment site within a coronary blood vessel (blood vessel 517).

In one embodiment, catheter assembly 500 includes primary cannula 512 having a link that extends from proximal portion 513 (e.g., located external to a patient during a procedure) to connect to the proximal end or skirt of balloon 520. Primary cannula 512 has a lumen therethrough that includes inflation cannula 528 and delivery cannula 530. Each of the inflation cannula 528 and delivery cannula 530 extend from proximal portion 513 of catheter assembly 500 to distal portion 514. Inflation cannula 528 has a distal end that terminates in balloon 520. Delivery cannula 530 extends through balloon 520 (i.e., beyond a distal end or skirt of balloon 520).

Catheter assembly 500 also includes guidewire cannula 516 extending, in this embodiment, through balloon 520 to a distal end of catheter assembly 500. Guidewire cannula 516 has a lumen sized to accommodate a guidewire (not shown). Catheter assembly 500 may be an over-the-wire (OTW) configuration where guidewire cannula 516 extends from a proximal end (external to a patient during a procedure) to a distal end of catheter assembly 500. In another embodiment, catheter assembly 500 is a rapid exchange (RX) type catheter assembly where only a portion of catheter assembly 500 (a distal portion including balloon 520) is advanced over the guidewire. FIG. 10 shows an OTW type catheter assembly.

In one embodiment, catheter assembly is introduced into blood vessel 517 in a direction of blood flow, such as through a femoral artery to a location within a coronary artery. Once introduced, balloon 520 is inflated (e.g., with a suitable liquid through inflation cannula 528) to occlude a blood vessel. Following occlusion, a treatment agent including a cellular component is introduced through delivery cannula 530. FIG. 10 shows treatment agent 550 that may be connected to delivery port 544 and introduced into delivery cannula 530. As noted above, in one embodiment, the delivery of treatment agent 550 will be with the flow of blood through the blood vessel. In one embodiment, it may be desirable to introduce the treatment agent so that the treatment agent flows through a blood vessel into capillary beds associated with the myocardium where it may induce and/or modulate angiomyogenesis. In another embodiment, it may be desired to introduce the treatment agent to aid in the repair of a damaged blood vessel, such as for example, occurs with an angioplasty procedure. In such case, the cellular component may be delivered so that it contacts the luminal surface of a blood vessel wall, such as for example, the cellular component of endothelial cells or endothelial progenitor cells that may function to stimulate the regrowth of a damage endothelial lining. To retain a treatment agent within a location in a blood vessel for at least a minimum period of time, it may be desirable to insert a balloon distal to an injury site distal to a treatment site and distal to a distal port of delivery cannula 530. The distal balloon may be part of catheter assembly 500 (e.g., a dual balloon catheter) or a part of the guidewire (e.g., a PERCU-SURG™ catheter assembly, commercially available from Medtronic, Inc. of Minneapolis, Minn.).

In another embodiment, a catheter assembly may be introduced into a blood vessel in a retrograde fashion so that the delivery of a treatment agent such as a cellular component will be against the blood flow. Various retrograde catheter assembly are described in U.S. patent application Ser. No. 10/387,048, filed Mar. 12, 2003 and titled, "Retrograde Pressure Regulated Infusion," commonly-assigned and U.S. patent application Ser. No. 10/800,323, filed Mar. 11, 2004 and titled, "Infusion Treatment Agents, Catheters, Filter Devices, and Occlusion Devices, and Use Thereof," which are each incorporated herein by reference. Representatively, a catheter assembly is introduced into a peripheral vein, such as a femoral vein and is guided through the right atrium into the coronary sinus. The catheter assembly may have a balloon that is positioned in the coronary sinus and expanded to occlude flow. A treatment agent including a cellular component may then be introduced under sufficient pressure so that the treatment agent can be forced to pass through the coronary sinus, through the capillary beds and the myocardium, and optionally through coronary arteries and ostia associated with respective coronary arteries into the ascending aorta.

Figure 11:
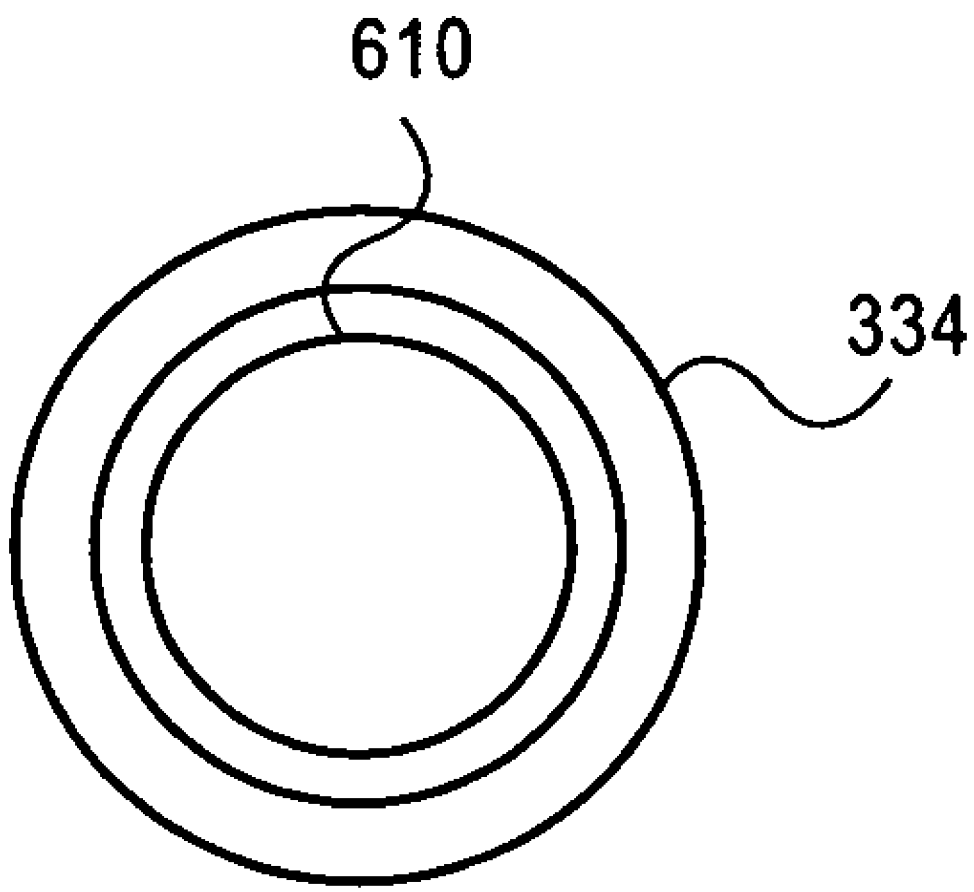
FIG. 11 shows a cross-sectional side view of a portion of an embodiment of a treatment agent delivery cannula of FIG. 4.

Thus far, embodiments have been described wherein a treatment agent including a cellular component may be encapsulated (totally or partially) in a viability enhancing material such as a hydrogel (e.g., PhosPEG-dMA macromer). The encapsulation seeks, in one embodiment, to improve the viability of the treatment agent at a treatment site by minimizing the contact between the cellular component and the delivery cannula (e.g., needle, etc.). In another embodiment, a viability enhancing material, such as a PhosPEG-dMA, may be coated on the luminal surface of a delivery cannula (e.g., needle) in an effort to improve the viability of the cellular component delivery through the delivery cannula. Representatively, a viability enhancing material such as a PhosPEG-dMA hydrogel coated on a luminal side of a delivery cannula tends to reduce the sheer stress on a treatment agent including a cellular component introduced through the delivery cannula. The reduction in the sheer stress would tend to improve the delivery viability and efficiency. FIG. 11 shows a cross-section of needle 334 (e.g., see FIG. 4). In one embodiment, needle 334 is a non-lubricious material such as a metallic material (e.g., stainless steel, Nitinol) or a high strength polymer. Needle 334 is configured to be retained in delivery cannula 330 during a procedure in which catheter assembly 330 is inserted into a body (e.g., blood vessel) of a patient. Needle 334 has a proximal end configured for attaching to a fluid delivery source and a pointed distal tip configured to pierce tissue. Needle 334 is sized to be slidably disposed within delivery cannula 330 so that a distal end of needle 334 may be advanced beyond a distal end of delivery cannula 330 and into tissue. In this embodiment, a luminal wall of needle 334 is coated with viability enhancing material 610. The viability enhancing material will have a lower coefficient of friction than a material for needle 334.

One way of coating a luminal surface of needle 334 is by dipping the delivery cannula in a macromer solution of a polymer and allowing the polymer to polymerize on the luminal surface. In one embodiment, the viability enhancer material is adhered onto the surface physically and is not chemically-bonded thereto. No surface treatment of an inner luminal surface of needle 334 is necessary and no primer pre-coating is required. The viability enhancer material need not be uniform or uniformly thick along a luminal surface of needle 334. It is also acceptable that some of the viability enhancer material sluffs off with a treatment agent delivered through needle 334.

A coated luminal surface of a delivery cannula may be used as an alternative to encapsulating a treatment agent including a cellular component or in addition to encapsulating the treatment agent. As a coating, the viability enhancing material improves not only cell viability but also enhances the lubricity along the lumen of needle 334 for effortless delivery of cells due to the lubricious nature of the viability enhancer material.

The following example describes one method for encapsulating HMSCs to make the encapsulated HMSCs suitable for percutaneous catheter delivery from, for example, a remote site such as a femoral or radial artery to a coronary treatment site.

Example (a) Cell Culturing

POIETICS™ hMSCs provided by Cambrex Inc. of Baltimore, Md. are thawed upon receipt and plated at 5,000 to 6,000 cells per square centimeter (cells/cm$^2$), in mesenchymal stem cell growth medium (MSCGM), a preservative medium for growing large numbers of mesenchymal stem cells without inducing differentiation by providing nutrients such as inorganic salts, amino acids, vitamins etc. The cells are harvested when they reach 80 to 90 percent confluence with trypsin and replated at 5,000 cells/cm$^2$. Passage 4 cells are trypsinized and harvested by centrifuge (1,000 rpm, 5 to 10 minutes). The supernatant is then discarded.

In the above discussion, the term "passage" means the cells that experience one cycle of culture process steps. The thawing of cells and culture processes include cell seeding, add the appropriate amount of medium to the vessel and allow the vessel to incubate for at least 30 minutes. Freshly thawed and primary cultured cells are considered passage 2. In this example, the numbers of hMSC cells were grown and expanded to passage 4. The passage procedure is typically initiated when the cells are about 80 percent confluent. Each culturing passage takes about two to four days to grow the cells to no more than 80 percent confluence before passing and readying to subculture. Representatively, each aliquot (vial) of cells should be passed for no more than six additional passages (total passage number 10). This passage number limit is based on significant changes in transfection efficiency beyond 10 passages. Maximal passage numbers could be subject to change if variation is noted in components as a function of passage numbers.

(b) Encapsulation

One-half to five percent PhosPEG-dMA macromer is prepared in a phosphate-buffered saline (PBS) solution at pH 7.4. The macromer solution is added to the re-suspended cells. A desired amount of cross-linker may be added to the macromer solution. Representative amounts of cross-linker depend on the desired polymerization. Each gel-construct was prepared with 75 microliter macromer solution encapsulating hMSCs (25 milliliter). The construct may be transferred into MSGGM medium and incubated at 37° C. in an inert atmosphere (e.g., five percent carbon dioxide ($CO_2$) atmosphere).

Since the hMSCs are contact-inhibited and are typically subcultured when they are just sub-confluent (about 90 percent confluent), supplementing a buffer medium such as phosphate buffered saline (PBS) with BSA or antibiotics penicillin/strptomycin or fetal bovine serum (FBS) may maintain and feed the hMSC culture after plating.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method comprising:
providing a cellular component having a property that can provide an angiogenic response;
providing a biodegradable viability enhancer material comprising a cross-linked hydrogel;
combining the cellular component and the viability enhancer material such that the viability enhancer material encapsulates the cellular component such that the combination will inhibit an interaction between the cellular component and a delivery device;
introducing the combination in a gel form suitable for delivery through the delivery device into a proximal portion of the delivery device; and
transluminally delivering the combination in the gel form to one or more of a vessel and a tissue through a needle at a distal portion of the delivery device,
wherein the delivery device is positioned within the vessel and the needle is advanced through a wall of the vessel to direct a flow of the liquid into the vessel or tissue.

2. The method of claim 1, wherein the cellular component comprises a stem cell.

3. The method of claim 1, wherein combining comprises coating the cellular component with the viability enhancer material.

4. The method of claim 1, wherein the delivery device comprises a percutaneously inserted transluminal catheter.

5. The method of claim 1, wherein the hydrogel is cross-linked through a chemical cross-linker.

6. The method of claim 1, wherein delivering the combination comprises delivering the combination beyond the vessel.

7. The method of claim 1, wherein the delivery device is advanced into a ventricle and delivering the combination comprises puncturing the ventricle and delivering the combination into a myocardial tissue.

8. The method of claim 1, wherein the hydrogel comprises phosphatidyl (ethylene glycol) methacrylate.

9. The method of claim 1, wherein the hydrogel is cross-linked through a photo-initiated cross-linker.

* * * * *